(12) United States Patent
Kimura et al.

(10) Patent No.: US 6,225,505 B1
(45) Date of Patent: May 1, 2001

(54) TRIFLUORO METHYLTHIOMETHYL BENZENE DERIVATIVES AND PROCESS FOR PRODUCTION SAME

(75) Inventors: Yoshikazu Kimura; Hidetaka Hiyoshi; Keiji Toriyabe; Nobuhide Wada, all of Shizuoka (JP)

(73) Assignees: Ihara Chemical Industry Co., LTD; Kumiai Chemical Industry Co., LTD, both of Tokyo (JP)

( * ) Notice: Subject to any disclaimer, the term of this patent is extended or adjusted under 35 U.S.C. 154(b) by 0 days.

(21) Appl. No.: 09/463,845

(22) PCT Filed: May 31, 1999

(86) PCT No.: PCT/JP99/02884

§ 371 Date: Feb. 1, 2000

§ 102(e) Date: Feb. 1, 2000

(87) PCT Pub. No.: WO99/62874

PCT Pub. Date: Dec. 9, 1999

(30) Foreign Application Priority Data

Jun. 1, 1998 (JP) .................................................. 10-167752

(51) Int. Cl.⁷ .................................................. C07C 319/14
(52) U.S. Cl. .................................. 568/56; 568/38; 568/41; 568/42; 568/43; 568/58
(58) Field of Search .................................. 568/38, 41, 42, 568/43, 56, 58

(56) References Cited

FOREIGN PATENT DOCUMENTS 8-295663   11/1996   (JP) .
9-3038      1/1997   (JP) .

OTHER PUBLICATIONS

CA:126:74605 abs of JP08295663, Nov. 1996.*
CA:131:170133 abs of J Fluorine Chem Taverner et al 95(1–2), pp. 171–176, 1999.*
CA:127:358694 abs of J Fluorine Chem 85(2) by Clark et al, pp. 169–172, 1997.*
Sheppard, W. A.; "Substituted Methyl Groups"; *Tetrahedron*; Int'l, J. Org. Chem.; vol. 27, pp. 95–951; (1971).

* cited by examiner

*Primary Examiner*—Jean F. Vollano
(74) *Attorney, Agent, or Firm*—Kubovcik & Kubovcik

(57) ABSTRACT

The present invention lies in a process for producing a trifluoromethylthiomethylbenzene derivative represented by the following general formula (2):

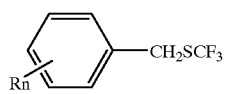

(2)

(wherein R is a hydrogen atom, a halogen atom, an alkyl group, an alkoxy group, an alkoxycarbonyl group, a cyano group, a nitro group, or a benzoyl group which may be substituted with halogen atom, alkyl group, alkoxy group, aliphatic or aromatic acyl group, nitro group, cyano group or alkoxycarbonyl group; n is an integer of 1 to 5; when n is an integer of 2 or more, a plurality of R's may be the same of each independently different), which process comprises reacting, in acetonitrile, a benzyl halide derivative represented by the following general formula (1):

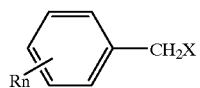

(1)

(wherein R and n have the same definitions as given above; and X is a halogen atom, an alkylsulfonyloxy group or an arylsulfonyloxy group which may be substituted with alkyl group or halogen atom) with thiophosgene and potassium fluoride.

2 Claims, No Drawings

TRIFLUORO METHYLTHIOMETHYL BENZENE DERIVATIVES AND PROCESS FOR PRODUCTION SAME

This application is the national phase of PCT/JP99/02884, filed May 31, 1999, now WO99/62874.

TECHNICAL FIELD

The present invention relates to a trifluoromethylthiomethylbenzene derivative useful as an intermediate for synthesis of pharmaceuticals and agrochemicals, as well as to a process for production thereof.

BACKGROUND ART

For production of a trifluoromethylthiomethylbenzene derivative, there have been known, for example, (1) a method of reacting a benzylmercaptan derivative or a benzyl thiocyanate derivative with sodium or potassium trifluoroacetate (JP-A-8-319251), (2) a method of reacting said derivative with trifluoromethyltrimethylsilane [Tetrahedron Letters, (1997) 38, 65), (3) a method of reacting said derivative with iodinated or brominated trifluoromethane and zinc (European Patents EP-742202 and EP-247953), (4) a method of reacting a benzyl halide derivative with a trifluoromethane thiol copper complex [Chem. Ber., (1988) 121, 1833; J. Org. Chem., (1976) 41, 1644], (5) a method of reacting a benzyl halide derivative with trifluoromethanesulfenyl chloride (U.S. Pat. No. 3,347,765), and (6) a method of reacting a benzyl halide derivative with bistrifluoromethane disulfide (Synthesis, 1994, 145).

In the method (1), however, the selectivity of intended substance is low and it is difficult to produce a trifluoromethylthiomethylbenzene derivative at a satisfactory yield; in the methods (2) to (4) which use a reagent made from a trifluoromethyl halide (flon) as basic raw material which is an ozone layer-destructing substance and an global-warming gas, the reagent is not suitable industrially because the raw material thereof is difficult to procure in recent years; in the methods (5) and (6), the reagent has a high toxicity and is difficult to procure industrially. Thus, the methods (1) to (6) have had various difficulties in industrial production of trifluoromethylthiomethylbenzene derivative.

The present invention has a main object of providing a process which can produce a trifluoromethylthiomethylbenzene derivative industrially at a high yield at a high purity without using a flon which is an ozone layer-destructing substance and an global-warming gas.

DISCLOSURE OF THE INVENTION

The present inventors made a study and found out that a trifluoromethylthiomethylbenzene derivative can be produced at a high yield by using, as a reagent, potassium trifluoromethylthiolate produced from a reaction system of thiophosgene and potassium fluoride.

The present inventors also found out that the trifluoromethylthiomethylbenzene derivatives produced by the process of the present invention include compounds which are useful as an intermediate for synthesis of pharmaceuticals and agrochemicals and which are novel.

The present invention provides a process for producing a trifluoromethylthiomethylbenzene derivative represented by the following general formula (2):

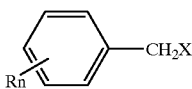
(2)

(wherein R is a hydrogen atom, a halogen atom, an alkyl group, an alkoxy group, an alkoxycarbonyl group, a cyano group, a nitro group, or a benzoyl group which may be substituted with halogen atom, alkyl group, alkoxy group, aliphatic or aromatic acyl group, nitro group, cyano group or alkoxycarbonyl group; n is an integer of 1 to 5; when n is an integer of 2 or more, a plurality of R's may be the same or each independently different), which process comprises reacting, in acetonitrile, a benzyl halide derivative represented by the following general formula (1):

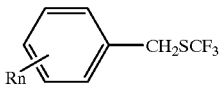
(1)

(wherein R and n have the same definitions as given above; and X is a halogen atom, an alkylsulfonyloxy group or an arylsulfonyloxy group which may be substituted with alkyl group or halogen atom) with thiophosgene and potassium fluoride.

The present invention also provides the following trifluoromethylthiomethylbenzene derivatives represented by the general formula (2):

2-fluoro-trifluoromethylthiomethylbenzene,
2-chloro-trifluoromethylthiomethylbenzene,
2-bromo-trifluoromethylthiomethylbenzene,
2-cyano-trifluoromethylthiomethylbenzene,
3-fluoro-trifluoromethylthiomethylbenzene,
3-chloro-trifluoromethylthiomethylbenzene,
3-bromo-trifluoromethylthiomethylbenzene,
3-cyano-trifluoromethylthiomethylbenzene,
4-cyano-trifluoromethylthiomethylbenzene,
4-methoxycarbonyl-trifluoromethylthiomethylbenzene,
4-ethoxycarbonyl-trifluoromethylthiomethylbenzene,
4-(n-propoxycarbonyl)-trifluoromethylthiomethylbenzene,
4-nitro-trifluoromethylthiomethylbenzene,
2-chloro-4-(trifluoromethylthiomethyl)benzophenone, and
3-chloro-4-(trifluoromethylthiomethyl)benzophenone.

The benzyl halide derivative used in the present process can be any compound represented by the general formula (1). In the general formula (1), R can be a hydrogen atom; a halogen atom (specific examples can be a chlorine atom, a bromine atom, an iodine atom and a fluorine atom. Hereinafter, "halogen atom" has the same meaning); an alkyl group (specific examples can be alkyl groups having 1 to 6 carbon atoms, such as methyl group, ethyl group, n-propyl group, isopropyl group, n-butyl group, isobutyl group, tert-butyl group, sec-butyl group, n-pentyl group, n-hexyl group and the like. Hereinafter, "alkyl group" has the same meaning); an alkoxy group (specific examples can be alkoxy groups having 1 to 6 carbon atoms such as methoxy group, ethoxy group, n-propoxy group, isopropoxy group, n-butoxy group, isobutoxy group, tert-butoxy group, sec-butoxy group, n-pentyloxy group, n-hexyloxy group and the like. Hereinafter, "alkoxy group" has the same meaning); an alkoxycarbonyl group [specific examples can be ($C_{1-6}$ alkoxy)-CO— groups such as methoxycarbonyl group, ethoxycarbonyl group, n-propoxycarbonyl group, isopropoxycarbonyl group, n-butoxycarbonyl group, isobutoxycarbonyl group, tert-butoxycarbonyl group, sec-butoxycarbonyl group, n-pentyloxycarbonyl group, n-hexyloxycarbonyl group and the like. Hereinafter, "alkoxycarbonyl group" has the same meaning]; a cyano group; a nitro group; or a benzoyl group which may be substituted with halogen atom, alkyl group, alkoxy group, aliphatic or aromatic acyl group (specific examples can be acetyl group, propionyl group, butyryl group and benzoyl group), nitro group, cyano group or alkoxycarbonyl group. When n is an integer of 2 or more, a plurality of R's may be the same or each independently different.

In the general formula (1), the substituent represented by X can be a halogen atom; an alkylsulfonyloxy group or an arylsulfonyloxy group which may be substituted with alkyl group or halogen atom.

As the benzyl halide derivative represented by the general formula (1), having such substituents Rn and X, there can be mentioned, for example, benzyl chloride, benzyl bromide, 4-chlorobenzyl chloride, 4-chlorobenzyl bromide, 2-chlorobenzyl chloride, 4-chloromethylbenzophenone, 4-chloromethyl-4'-chlorobenzophenone, 4-bromomethyl-4'-chlorobenzophenone, 4-chloromethyl-4'-methylbenzophenone, 4-chloromethyl-2'-chlorobenzophenone, 2-chloromethyl-4'-chlorobenzophenone, 2,4-dichlorobenzyl chloride, 2,4-dichlorobenzyl bromide, 3,4-dichlorobenzyl chloride, 3,4-dichlorobenzyl bromide, 4-methylbenzyl chloride, 4-methoxybenzyl chloride, 4-cyanobenzyl chloride, 4-nitrobenzyl chloride, 2,4-dinitrobenzyl chloride, 2,4-dinitrobenzyl bromide, 4-methoxycarbonylbenzyl chloride, 4-ethoxycarbonylbenzyl chloride, 4-chlorobenzyl methanesulfonate, 4-chlorobenzyl p-toluenesulfonate and 4-chlorobenzyl p-chlorobenzenesulfonate.

In the present process, the amount of thiophosgene used can be 1 to 3 equivalents relative to the benzyl halide derivative represented by the general formula (1).

In the present process, the amount of potassium fluoride used can be 3 to 9 equivalents relative to thiophosgene.

In the present process, acetonitrile is used as a solvent. This acetonitrile must be dehydrated, and it is preferred to use acetonitrile after drying with a desiccant, for example, Molecular Sieves 3A.

The amount of acetonitrile used can be 2 to 10 liters, preferably 4 to 8 liters per mole of the benzyl halide derivative represented by the general formula (1).

In the present process, the reaction temperature is −20 to 70° C., preferably 0 to 30° C.

The trifluoromethylthiomethylbenzene derivatives represented by the general formula (2), which are intended compounds, can be isolated by an ordinary method and include the following novel compounds not described in any literature:

2-fluoro-trifluoromethylthiomethylbenzene,
2-chloro-trifluoromethylthiomethylbenzene,
2-bromo-trifluoromethylthiomethylbenzene,
2-cyano-trifluoromethylthiomethylbenzene,
3-fluoro-trifluoromethylthiomethylbenzene,
3-chloro-trifluoromethylthiomethylbenzene,
3-bromo-trifluoromethylthiomethylbenzene,
3-cyano-trifluoromethylthiomethylbenzene,
4-cyano-trifluoromethylthiomethylbenzene,
4-methoxycarbonyl-trifluoromethylthiomethylbenzene,
4-ethoxycarbonyl-trifluoromethylthiomethylbenzene,
4-(n-propoxycarbonyl)-trifluoromethylthiomethylbenzene,
4-nitro-trifluoromethylthiomethylbenzene,
2-chloro-4-(trifluoromethylthiomethyl)benzophenone, and
3-chloro-4-(trifluoromethylthiomethyl)benzophenone.

BEST MODE FOR CARRYING OUT THE INVENTION

The present invention is described specifically below by way of Examples.

EXAMPLE 1

A mixture consisting of 1.0 g (17.8 mmol) of spray-dried potassium fluoride, 1.30 g (4.2 mmol) of 4-bromomethyl-4'-chlorobenzophenone and 30 ml of dry acetonitrile was cooled to 0° C. in a nitrogen atmosphere. Thereto was added 0.4 ml (5.1 mmol) of thiophosgene. The resulting mixture was stirred at 0° C. for 2 hours and then at room temperature for 8 hours. After the completion of the reaction, 20 ml of a saturated aqueous sodium hydrogencarbonate and 20 ml of ethyl acetate were added. The organic layer was separated and dried over anhydrous sodium sulfate. The resulting organic layer was subjected to distillation to remove the solvent to obtain 1.37 g (yield=98.8%) of 4-trifluoromethylthiomethyl-4'-chlorobenzophenone as red crystals. The crystals were washed with cold hexane to obtain light yellow crystals.

GC-MS: 332 ($M^+$+2), 330 ($M^+$), 229 (Base)

Melting point: 67 to 69° C. [values in literatures: 63 to 65° C. (JP-A-9-3038); 78 to 79° C. (JP-A-9-278744)]

EXAMPLE 2

1.0 g (17.8 mmol) of spray-dried potassium fluoride and 0.82 g (4.2 mmol) of 4-cyanobenzyl bromide were placed in 30 ml of dry acetonitrile. The mixture was stirred in an ice bath of 0° C. Thereto was dropwise added, in 5 minutes, 0.4 ml (5.1 mmol) of thiophosgene using a syringe. The resulting mixture was stirred in an ice bath of 0° C. for 1 hour and then at room temperature for 18 hours. Part of the reaction mixture was monitored by gas chromatography, which indicated the formation of 59% of 4-cyano-trifluoromethylthiomethylbenzene and the presence of residual 4-cyanobenzyl bromide. Therefore, the above reaction was continued. The reaction was conducted for total 42 hours. To the reaction mixture were added 20 ml of a saturated aqueous sodium hydrogencarbonate and 20 ml of ethyl acetate. The resulting mixture was subjected to extraction, phase separation, drying and vacuum distillation (for removal of solvent) to obtain 0.83 g of a yellow liquid. The liquid was subjected to gas chromatography, which indicated that 91% of 4-cyano-trifluoromethylthiomethylbenzene was formed and 9% of the raw material was converted into 4-cyanobenzyl chloride. GC-MS detected ion peaks of respective molecules and supported their structures.

4-Cyano-trifluoromethylthiomethylbenzene: m/z=217 ($M^+$)

Industrial Applicability

The present invention is a useful process which can produce a trifluoromethylthiomethylbenzene derivative useful as an intermediate for synthesis of pharmaceuticals and agrochemicals, at a high yield at a high purity using an industrially available raw material and without using a flon which is an ozone layer-destructing substance and an global-warming gas.

The present invention further can provide a trifluoromethylthiomethylbenzene derivative which is useful as an intermediate for synthesis of pharmaceuticals and agrochemicals and which is new.

What is claimed is:

1. A process for producing a trifluoromethylthiomethylbenzene derivative represented by the following formula (2):

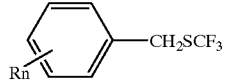
(2)

(wherein R is a hydrogen atom, a halogen atom, an alkyl group, an alkoxy group, an alkoxycarbonyl group, a cyano group, a nitro group, or a benzoyl group which may be substituted with halogen atom, alkyl group, alkoxy group, aliphatic or aromatic acyl group, nitro group, cyano group or alkoxycarbonyl group; n is an integer of 1 to 5; when n is an integer of 2 or more, a plurality of R's may be the same or each independently different), which process comprises reacting, in acetonitrile, a benzyl halide derivative represented by the following formula (1):

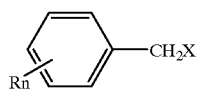
(1)

(wherein R and n have the same definitions as given above; and X is a halogen atom, an alkylsulfonyloxy group or an arylsulfonyloxy group which may be substituted with alkyl group or halogen atom) with thiophosgene and potassium fluoride.

2. The following trifluoromethylthiomethylbenzene derivatives 2-fluoro-trifluoromethylthiomethylbenzene,
2-chloro-trifluoromethylthiomethylbenzene,
2-bromo-trifluoromethylthiomethylbenzene,
2-cyano-trifluoromethylthiomethylbenzene,
3-chloro-trifluoromethylthiomethylbenzene,
3-bromo-trifluoromethylthiomethylbenzene,
3-cyano-trifluoromethylthiomethylbenzene,
4-cyano-trifluoromethylthiomethylbenzene,
4-methoxycarbonyl-trifluoromethylthiomethylbenzene,
4-ethoxycarbonyl-trifluoromethylthiomethylbenzene,
4-(n-propoxycarbonyl)-trifluoromethylthiomethylbenzene,
4-nitro-trifluoromethylthiomethylbenzene,
2-chloro-4-(trifluoromethylthiomethyl)benzophenone, and
3-chloro-4-(trifluoromethylthiomethyl)benzophenone.

\* \* \* \* \*